(12) United States Patent  (10) Patent No.: US 6,723,097 B2
Fraser et al.  (45) Date of Patent: Apr. 20, 2004

(54) SURGICAL TRIAL IMPLANT

(75) Inventors: Robert Fraser, Myrtle Bank (AU);
Mark Boomer, Somerville, MA (US)

(73) Assignee: DePuy Spine, Inc., Raynham, MA (US)

( * ) Notice: Subject to any disclaimer, the term of this patent is extended or adjusted under 35 U.S.C. 154(b) by 0 days.

(21) Appl. No.: 10/200,890

(22) Filed: Jul. 23, 2002

(65) Prior Publication Data

US 2004/0019356 A1 Jan. 29, 2004

(51) Int. Cl.[7] ............................................... A61B 17/70
(52) U.S. Cl. ........................................ 606/61; 623/17.11
(58) Field of Search .......................... 623/17.11–17.16, 623/16.11; 606/61, 69, 79, 86, 97, 102

(56) References Cited

U.S. PATENT DOCUMENTS

| 4,795,463 A | * | 1/1989 | Gerow ............................. 623/8 |
| 4,834,757 A | | 5/1989 | Brantigan |
| 4,985,019 A | * | 1/1991 | Michelson ..................... 604/180 |
| 5,045,080 A | | 9/1991 | Dyer et al. ..................... 604/362 |
| 5,071,437 A | * | 12/1991 | Steffee, Arthur D. ..... 623/17.16 |
| 5,133,342 A | | 7/1992 | Seaton ............................ 602/39 |
| 5,361,766 A | | 11/1994 | Nichols et al. ............. 128/654 |
| 5,383,233 A | | 1/1995 | Russell ........................ 378/162 |
| 5,676,146 A | * | 10/1997 | Scarborough ............. 623/16.11 |
| 6,041,094 A | | 3/2000 | Russell .......................... 378/37 |
| 6,093,201 A | * | 7/2000 | Cooper et al. ................. 606/69 |
| 6,113,639 A | | 9/2000 | Ray et al. .................... 623/17.16 |
| 6,132,465 A | * | 10/2000 | Ray et al. .................... 623/17.16 |
| 6,146,422 A | | 11/2000 | Lawson |
| 6,200,258 B1 | | 3/2001 | Slater et al. .................... 600/8 |
| 6,264,695 B1 | * | 7/2001 | Stoy ............................. 623/17.16 |

FOREIGN PATENT DOCUMENTS

| WO | WO 96/00539 | 1/1996 |
| WO | WO 01/70144 | 9/2001 |

* cited by examiner

*Primary Examiner*—David O. Reip
(74) *Attorney, Agent, or Firm*—Nutter McClennen & Fish LLP

(57) ABSTRACT

A trial implant and trial implant kit for assisting a physician in selecting an appropriately sized prosthesis is provided. In one embodiment, the trial medical implant device includes a body formed from a radio-lucent material and having a size and shape adapted to fit within or adjacent to an interstitial space, and at least one marker associated with the body and formed from a radio-opaque material. The at least one marker is configured to provide an x-ray visible reference to indicate the position and/or alignment of the body with respect to an anatomical structure when the trial medical implant device is positioned within an interstitial space.

30 Claims, 6 Drawing Sheets

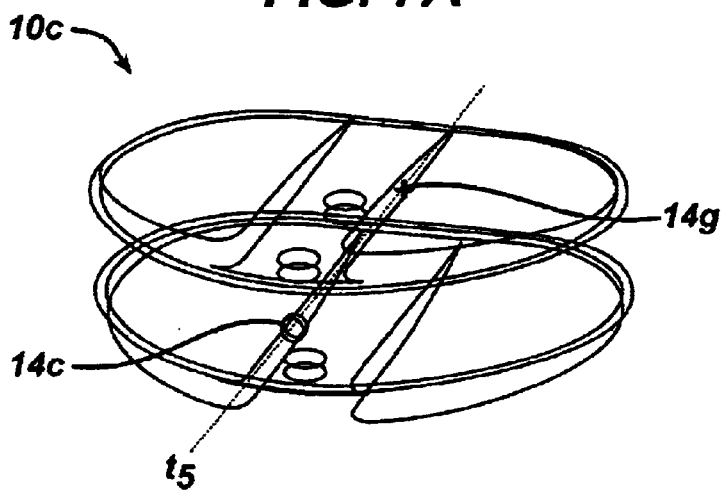
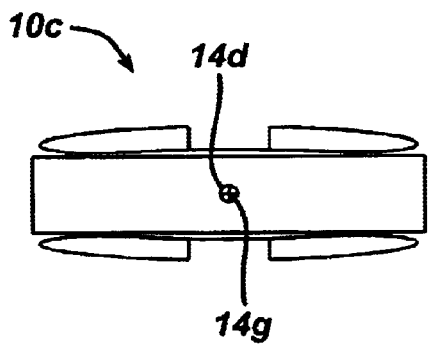
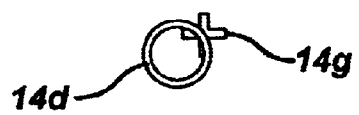

SURGICAL TRIAL IMPLANT

FIELD OF THE INVENTION

The present invention relates to a trial medical implant device, and more particularly, to a trial medical implant device for evaluating the size, shape, and alignment of the implant with respect to an anatomical structure. The present invention also relates to a method of manufacturing a trial implant device.

BACKGROUND OF THE INVENTION

Advancing age, as well as injuries, can lead to changes in the various bones, discs, joints and ligaments of the body. In particular, these changes can manifest themselves in the form of damage or degeneration of an intervertebral disc, the result of which is mild to severe chronic back pain. Intervertebral discs serve as "shock" absorbers for the spinal column, absorbing pressure delivered to the spinal column. Additionally, they maintain the proper anatomical separation between two adjacent vertebra. This separation is necessary for allowing both the afferent and efferent nerves to exit and enter, respectively, the spinal column.

Treatment for a diseased or damaged disc can involve the removal of the natural, damaged disk tissue, and the subsequent replacement of the disc with an implant, such as an interbody cage or fusion device, or a disc prosthesis. The implant should have an appropriate size and shape to complement the normal height of the disc and to contour the vertebral endplates adjacent the disc space to provide stability and, if a fusion device is being implanted, to promote fusion. If the shape of the vertebral endplates does not match the shape of the implant, shifting can occur resulting in misalignment of the vertebrae. Accordingly, it is important for the implant to correspond as closely as possible to the region of the intradiscal space that is receiving the implant.

Selection of a properly sized implant can be difficult due to the enclosed nature of the nucleus cavity. X-rays generally reveal very little about the particular size and shape of the intradiscal space, and thus surgeons often have to rely on an estimated shape and size based on physiological factors, such as the patient's height, weight, etc., as well as the position of the vertebrae. While this method can be sufficient, the selection of an improperly sized implant can lead to problems. An oversized implant, for example, will be difficult to position between the adjacent vertebrae and can lead to long term problems once implanted. Moreover, due to the enclosed nature of the nucleus cavity, it is virtually impossible for a surgeon to accurately evaluate the size and shape of the cavity, much less the matching of the implant with the vertebral endplates. Unfortunately, the sizing problem is not always discovered until the surgeon attempts to position the implant between the vertebrae. As a result, the implant will have been in direct contact with bodily fluids and will be contaminated. Some implants can be virtually impossible to resterilize due to the nature of the materials from which they are made. In such cases, it is necessary to discard an expensive device.

To overcome this problem, trial implants and trial implant kits have been developed to assist surgeons in selecting an implant having the appropriate size and shape. U.S. Pat. No. 6,113,639 of Ray et al. discloses, for example, a trial implant kit containing several trial implants, each sized and shaped to simulate the size and shape of an available prosthetic implant. The surgeon can select an implant from the kit to temporarily position within the disc space to evaluate the size of the intradiscal space and the fit of a sample prosthesis. A contrast material can be injected into the nucleus cavity to view the trial implant with respect to the intradiscal space via a fluoroscope.

While fluoroscopy or x-ray can be effective to verify the placement of a trial implant, the image produced can be distorted by the large, opaque implant. This distortion can either shield or completely obscure the anatomical matching that the surgeon desires to verify. It can also be difficult to accurately assess whether the implant is in close contact with the complex geometries of the adjacent vertebral endplates.

Accordingly, there is a need for a trial implant that can be used to accurately and effectively evaluate the size, shape, and alignment of the implant with respect to an anatomical structure.

SUMMARY OF THE INVENTION

The present invention provides a trial implant and trial implant kit for assisting a physician in selecting an appropriately sized prosthesis. In one embodiment, the trial medical implant device includes a body formed from a radio-lucent material and having a size and shape adapted to fit within or adjacent to an interstitial space, and at least one marker associated with the body and formed from a radio-opaque material. The at least one marker is configured to provide an x-ray visible reference to indicate the position and alignment of the body with respect to an anatomical structure when the trial medical implant device is positioned within an interstitial space.

The markers can be disposed on an outer surface of the body and/or embedded in the body. In one embodiment, the implant includes several markers, each of which can be selectively positioned to intersect to form one or more reference points on the body. Thus, when implanted in the body, an x-ray image can be used to determine the exact position of the implant with respect to an anatomical structure. In another embodiment, the implant can include first and second markers that are selectively distinguishable on an x-ray image. Each marker can have a variety of shapes, and can be in the form of a tube, cross, sphere, plate, ring, rod, T-shape, and combinations thereof.

In further aspects of the present invention, the body of the implant has a shape and size adapted to fit between adjacent vertebral bodies. By way of non-limiting example, the body can be a disc-shaped member having a superior, bone-contacting surface and an inferior, bone-contacting surface. The at least one marker is preferably effective to indicate the alignment of the superior and inferior bone-contacting surfaces of the body with respect to superior and inferior endplates of adjacent vertebral bodies when the implant is positioned between adjacent vertebral bodies.

In another embodiment of the present invention, a trial spinal implant is provided having a trial implant member formed from a radio-lucent material and having a size and shape configured to fit between adjacent vertebral bodies. The trial implant member includes a superior bone-contacting surface and an inferior bone-contacting surface. At least one marker formed from a radio-opaque material is associated with the trial implant member such that, when the trial implant is positioned between adjacent vertebral bodies, the at least one marker provides at least one x-ray visible reference to indicate the position and/or alignment of the implant with respect to the adjacent vertebral bodies. In a preferred embodiment, the superior and inferior bone-contacting surfaces of the trial implant member each have a shape adapted to conform to an endplate of an adjacent vertebral body. Thus, when implanted in the body, the at least one marker indicates, on an x-ray image, the alignment of the superior and inferior bone-contacting surfaces of the trial implant member with respect to the endplates of adjacent vertebral bodies.

In yet another embodiment of the present invention, a trial implant system is provided having a plurality of implantable trial prostheses. Each implantable prosthesis includes a body formed from a radio-lucent material and having a size and shape adapted to fit within or adjacent to an anatomical structure, and at least one marker associated with the body and formed from a radio-opaque material. The at least one marker is configured to provide an x-ray visible reference to indicate the position and alignment of the body with respect to the anatomical structure when the implantable trial prosthesis is positioned within or adjacent to an anatomical structure.

In other aspects of the present invention, a method for manufacturing a trial implant is provided. The method includes the steps of providing at least one marker formed from a radio-opaque material, providing a mold having a desired size and shape for a medical implant, strategically placing each of the at least one markers in the mold such that the markers are configured to provide at least one x-ray visible reference to indicate the size and shape of the medical implant, and injecting a radio-lucent material into the mold to form a trial implant.

BRIEF DESCRIPTION OF THE DRAWINGS

The invention will be more fully understood from the following detailed description taken in conjunction with the accompanying drawings, in which:

FIG. 7A illustrates a perspective view of yet another embodiment of a trial implant having several radio-lucent markers positioned around and/or within the implant;

FIG. 7B illustrates a front view of the trial implant of FIG. 7A; and

FIG. 7C illustrates a ring marker and a cross marker being misaligned with respect to each other.

DETAILED DESCRIPTION OF THE INVENTION

Figure 1:
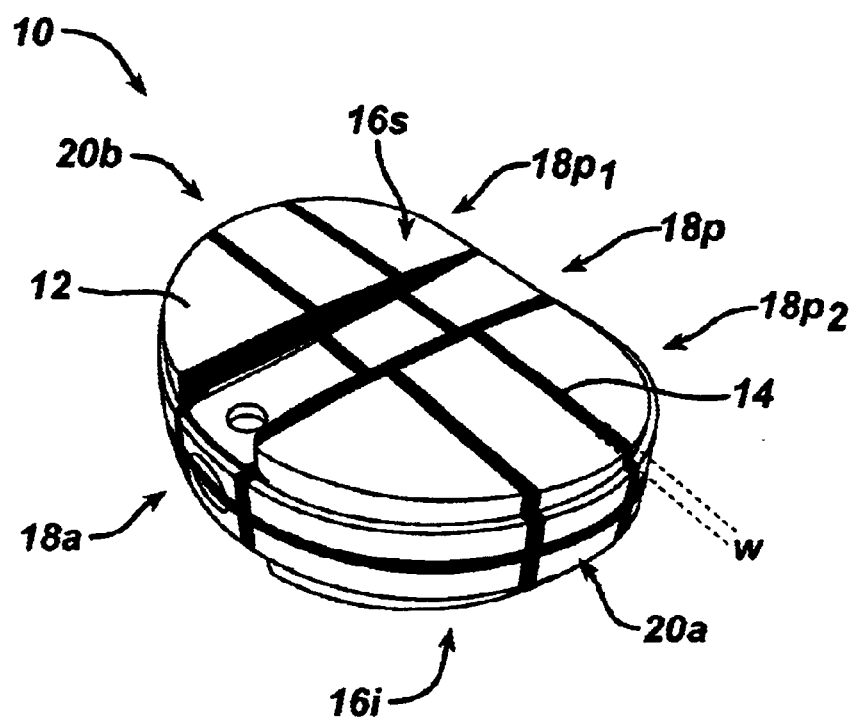
FIG. 1 is a anterior perspective view of a trial implant member according to one embodiment of the present invention.

The present invention provides a trial implant and trial implant kit for assisting a physician in selecting an appropriately sized prosthesis. The trial implant is effective to indicate, on an x-ray image, the shape, size, and/or position of the implant with respect to an anatomical structure when the implant is positioned within or adjacent the anatomical structure. As shown in FIG. 1, the implant 10 generally includes a body 12 formed from a radio-lucent material, and at least one marker 14 associated with the body 12 and formed from a radio-opaque material.

Figure 2A:
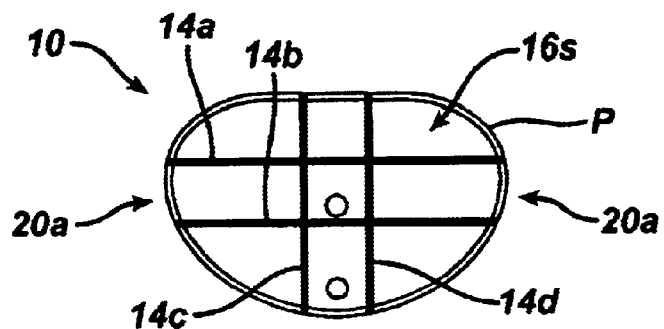
FIGS. 2A–2C are top, lateral side, and anterior side views, respectively, of the trial implant of FIG. 1.

The body of the trial implant can have virtually any configuration, depending on the intended use. The body should, however, have a size and shape adapted to fit within an interstitial space, and more preferably the size and shape of the body should be identical or at least similar to the size and shape of a prosthesis desired to be implanted into a patient. FIG. 1 illustrates one example of a trial implant 10 having a disc-shaped body 12 adapted to be positioned between adjacent vertebral bodies. The body includes superior and inferior surfaces 16s, 16i, posterior and anterior sides 18p, 18a, first and second lateral sides 20a, 20b, respectively, and a perimeter P (FIG. 2A). While the body 12 can have any shape, the posterior side 18p of the illustrated body 12 is preferably substantially flat, while the anterior side 18a and the first and second lateral sides 20a, 20b preferably form a curved convex portion of the perimeter P between opposite ends $18p_1$, $18p_2$ of the flattened posterior side 18p.

A person having ordinary skill in the art will appreciate that the superior and inferior surfaces 16s, 16i of the body 12 can have a variety of shapes, sizes, and/or features present on one of both of the surfaces 16s, 16i. By way of non-limiting example, one or both of the surfaces 16s, 16i can have a wedge-like shape (not shown) wherein one side (e.g., posterior) of the body 12 member has a height less than a height of the opposed side (e.g., anterior) of the body 12. Other profiles include, for example, a supine shape, a converging portion, and a domed or convex-like profile. One of ordinary skill in the art will appreciate that various combinations of these profiles may be used as well. Moreover, the trial implant can be adapted to be used with either unprepared or prepared bony endplates of adjacent vertebrae.

The trial implant 10 further includes one or more markers that are effective to indicate, on an x-ray image, the size, shape, and/or position of the implant 10 with respect to adjacent bone structures. The markers are formed from a radio-opaque material and can have virtually any shape and size. FIG. 1 illustrates one example of a trial implant 10 having several marker strips 14 that extend around the body 12. As shown, the marker strips 14 are formed from generally elongate strip-like members. Each strip 14 preferably has a width w sufficient to be detectable on an x-ray image. While the marker strips 14 are shown extending around the body 12, the marker strips 14 can alternatively, or in addition, have varying lengths and can be disposed at distinct positions on or within the body. For example, two marker strips 14 could be positioned to form an x-like marking to indicate a particular reference point on the body 12. A person having ordinary skill in the art will appreciate that the marker strips can vary in shape and size.

Figure 2B:
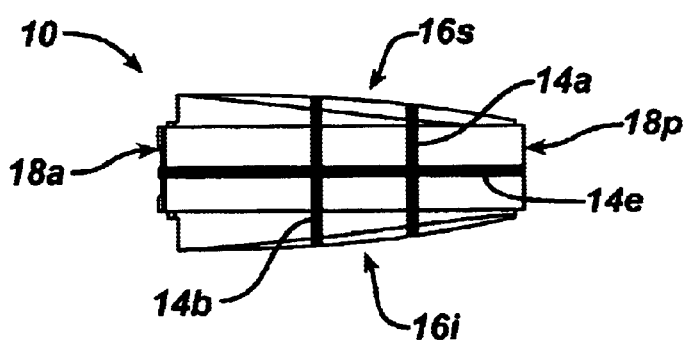
Figure 2C:
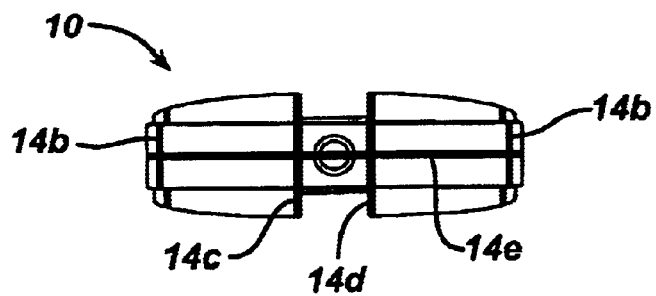

The position of the marker strips 14 on the body 12 can also vary, but preferably the strips 14 are strategically positioned around and/or within the body 12 of the implant 10 to assist a physician in assessing the size, shape, and/or alignment of the implant 10, via an x-ray image, with respect to bone structures surrounding an interstitial space. FIGS. 2A–2C, for example, illustrate implant 10 having five marker strips disposed around the body 12 to essentially outline the shape of the body 12. FIG. 2A illustrates a superior view of the implant having marker strips 14a and 14b extending around the implant 10 between the first and second lateral sides 20a, 20b of the implant, and having marker strips 14c and 14d extending around the posterior and anterior sides 18a, 18p of the implant 10. FIG. 2B illustrates a lateral side view of the implant having an additional marker strip 14e that extends around the perimeter p of the implant 10. FIG. 2C illustrates an additional, anterior view of the implant 10 having marker strips 14a–14e.

Figure 3:
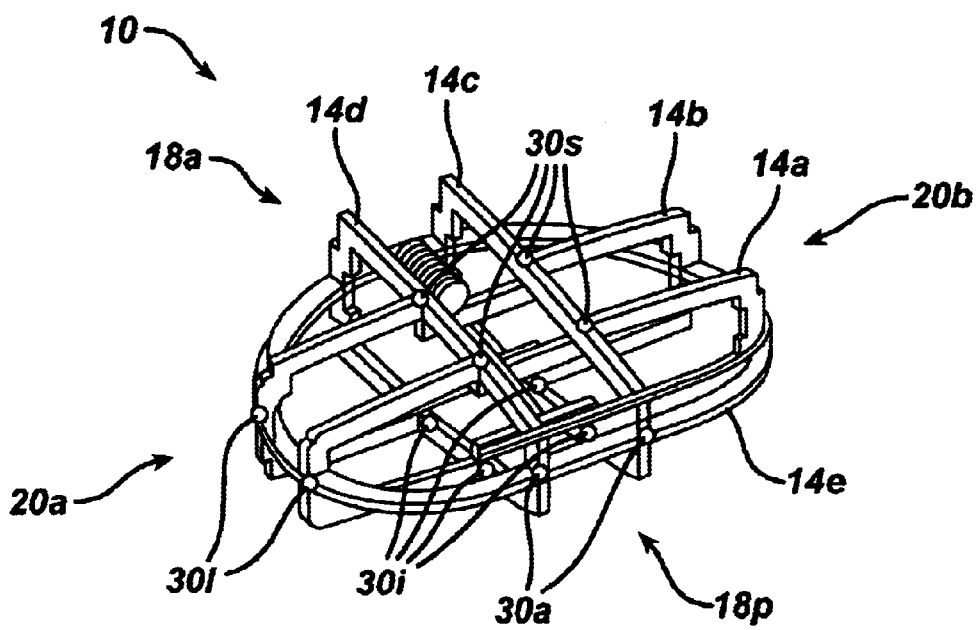
FIG. 3 is a posterior perspective view illustrating the radio-lucent marking strips of a trial implant member according to another embodiment of the present invention.

FIG. 3 illustrates an x-ray image of implant 10 having marker strips 14a–14e. As shown, marker strips 14c and 14d each extend around the implant 10 to form a generally rectangular object on the x-ray image. The corners of the marker strips can be used as reference points. The marker strips 14c and 14d further intersect with marker strips 14a and 14b to form additional reference points (shown as white dots for reference purposes). As shown, four reference points 30s are positioned on the superior surface 16s of the implant, and four reference points 30i are positioned on the inferior surface 16i of the implant 10. The implant 10 also includes two references points 30l on each of the lateral sides 20a, 20b, and two references points 30a on each of the anterior and posterior sides 18a, 18p.

Figure 4:
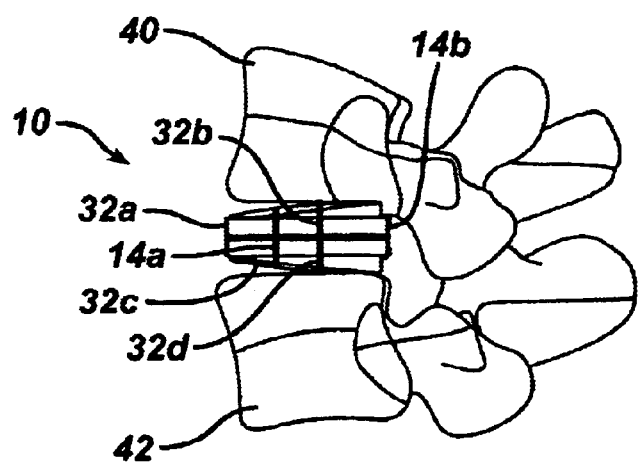
FIG. 4 is a side view illustration of a trial implant member positioned between adjacent vertebrae.

In use, the surgeon can determine the shape, size, and/or position of the implant with respect to adjacent vertebral bodies based on reference points determined by the intersection of two marker strips 14, as well as the shape of each marker strip 14. Several x-ray images can be taken to display particular reference points. FIG. 4 illustrates, for example, an implant 10 positioned between adjacent vertebrae 40, 42. As shown the corners of marker strips 14a and 14b form reference points 32a, 32b, 32c, and 32d, which can be used to verify the alignment of the implant 10 with respect to the endplates of the adjacent vertebrae 40, 42.

Figure 5A:
FIGS. 5A–5H illustrate several embodiments of markers for use with an implant according to the present invention.
Figure 5B:
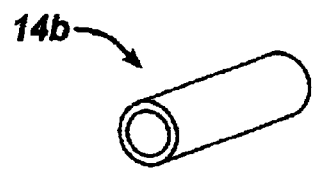
Figure 5C:
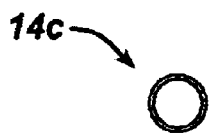
Figure 5D:
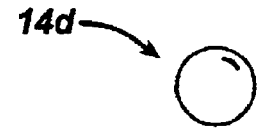
Figure 5E:
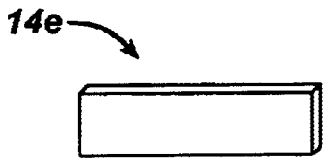
Figure 5F:
Figure 5G:
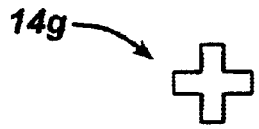
Figure 5H:

FIGS. 5A–5H illustrate additional embodiments of markers suitable for use with a trial implant. FIG. 5A illustrates a marker strip 14a, which is essentially the same as the marker strip shown in the implant of FIGS. 1–4. FIG. 5B illustrates a cylinder marker 14b, which is particularly useful in that an x-ray image of the cylinder marker 14b will appear as a circle if the implant is properly aligned. FIG. 5C illustrates a ring marker 14c. The ring marker 14c is preferably used as an alignment guide in combination with a marker having a different shape. In use, an x-ray image of the ring marker 14c can be used to align another marker in the center of the ring 14c. FIG. 5D illustrates another embodiment of a marker 14d having a spherical shape. The spherical marker 14d can be used in combination with other spherical markers 14d such that an x-ray image of a properly aligned implant having two spheres 14d positioned along an axis will display only a single sphere 14d. FIG. 5E illustrates a plate marker 14e having a substantially flattened rectangular shape. The plate marker 14e is particularly useful to indicate the angular relationship of the implant with respect to bone structures adjacent an interstitial space. The plate marker 14e is preferably used in combination with a ring marker 14c, cylinder marker 14b, or with additional plate markers 14e. FIG. 5F illustrates a rod marker 14f, which is also preferably used to indicate the angular relationship of the marker 14f with respect to bone structures adjacent an interstitial space. When the implant is properly aligned, the rod marker 14f will appear as a single point on an x-ray image. FIGS. 5G and 5H illustrate additional embodiments of markers. FIG. 5G illustrates a marker 14g in the shape of a cross, and FIG. 5H illustrates a T-shaped marker 14h. The cross and T-shaped markers 14g, 14h are preferably used in combination with the ring 14c, cylinder 14b, or spherical markers 14d, and will appear centered with respect to the other markers when properly aligned. Two T-shaped markers 14h can also be positioned along an axis and inverted with respect to each other such that an x-ray image of the markers 14h, when properly aligned, will illustrate a cross or the letter "H," depending on the position of the markers 14h. A person having ordinary skill in the art will appreciate that the markers of the present invention can have virtually any configuration and can be used in combination with any number of markers having the same or a different configuration.

In an exemplary embodiment, pairs of markers are positioned along a predetermined axis of the implant. An x-ray image, taken along a particular axis, can then be used to verify the alignment of the implant. If the implant is properly aligned, the pair of markers positioned along the axis will appear as a single marker, or will be displayed in some configuration indicative of alignment of the implant. The pairs of markers are preferably positioned on opposed sides of the implant to provide greater accuracy in alignment of the implant.

Figure 6A:
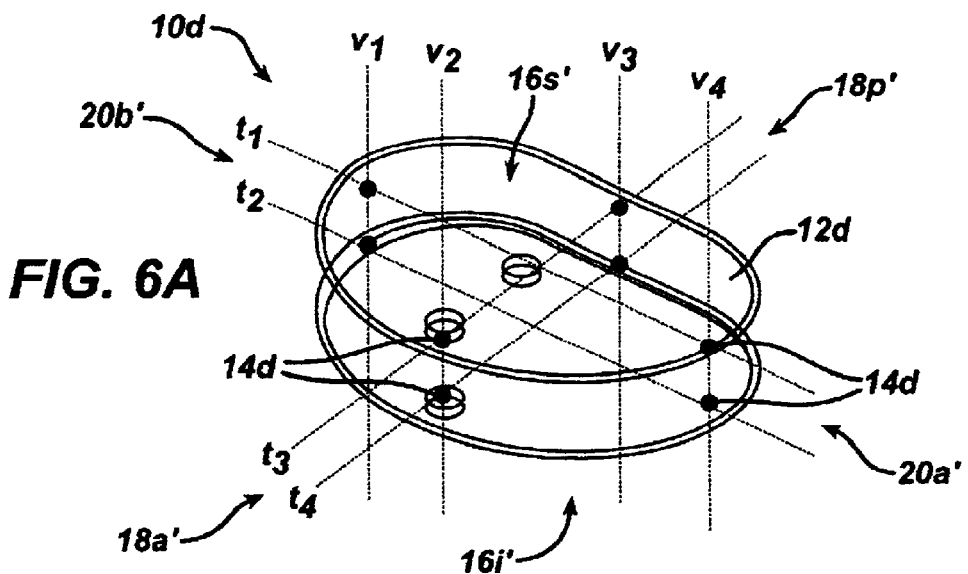
FIG. 6A illustrates a perspective view of another embodiment of a trial implant having several radio-lucent sphere markers positioned around and/or within the implant.
Figure 6B:
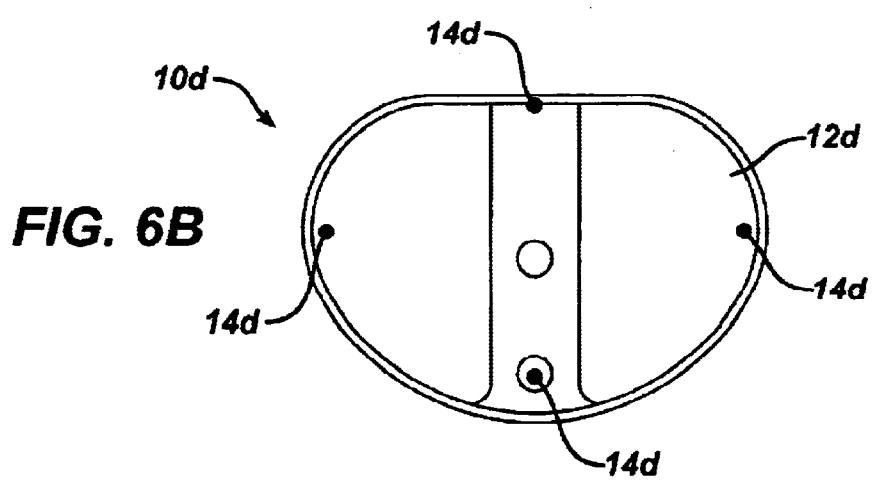
FIG. 6B illustrates a top view of the implant of FIG. 6A.
Figure 6C:
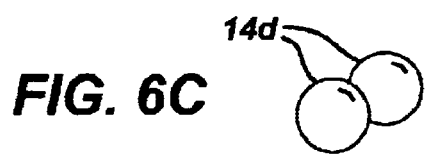
FIG. 6C illustrates two misaligned sphere markers.

FIG. 6A illustrates an exemplary embodiment of an implant 10d having a body 12d with several sphere-shaped markers 14d positioned in pairs throughout the body 12d along predetermined axes $t_{1-4}$, $v_{1-4}$. Axes $v_1$, $v_2$, $v_3$, and $v_4$ extend between the superior and inferior surfaces 16s', 16i', axes $t_3$ and $t_4$ extend between the posterior and anterior sides 18p', 18a', and axes $t_1$ and $t_2$ extend between the first and second lateral sides 20a', 20b'. Two markers are positioned along each axis, as shown. In use, each marker pair can be used to determine the proper alignment of the implant. FIG. 6B, for example, illustrates an x-ray image of a top view of the superior surface 16s' of the implant 10d. The pairs of markers that extend along axes $v_1$, $v_2$, $v_3$, and $v_4$ are each shown as a single marker 14d, thereby indicating that the implant is properly aligned. In the event the implant 10 is not properly aligned once implanted in a patient's body, the pairs of markers would each be displayed adjacent or offset from one another, as shown in FIG. 6C.

FIG. 7A illustrates another embodiment of a trial implant 10c having at least one pair of markers 14c, 14g positioned on opposed sides of the implant 10c along an axis $t_5$. As shown, one of the markers 14c is in the shape of a ring, and the opposed marker 14g is in the shape of a cross. FIG. 7B illustrates an x-ray image of the implant 10c taken along axis 15. The implant is properly aligned since the x-ray image illustrates the cross-shaped marker 14g centered within the ring-shaped marker 14c. FIG. 7C illustrates an example of the image of markers that is obtained in an improperly aligned implant in which the cross-shaped marker 14g is off-center with respect to the ring-shaped maker 14c.

The trial implant of the present invention can be provided as a system or kit containing several implantable trial implants. Each implant preferably has a different shape and/or size, which is identical to, or similar to, a shape and size of an available prosthesis to be implanted. Each trial implant includes a body formed from a radio-lucent material and having a size and shape adapted to fit within or adjacent to an anatomical structure, and at least one marker strip associated with the body and formed from a radio-opaque material. The marker strips are configured to indicate, on an x-ray image, the size and alignment of the body with respect to the anatomical structure when the implantable trial prosthesis is positioned within or adjacent to an anatomical structure. In use, the surgeon can select an implant from among several implants provided in the kit, and position and x-ray the implant to determine the fit. In the event that the selected trial implant does not fit appropriately, the surgeon can then select another implant from the kit. This process is repeated until the surgeon has selected the appropriately sized implant for that particular patient.

The trial implants of the present invention can be manufactured using a variety of techniques. In one embodiment, a trial implant can be manufactured by strategically placing at least one marker strip formed from a radio-opaque material into a mold having a desired size and shape for a medical implant. The marker strips are preferably positioned and configured to indicate, on an x-ray image, the size and shape of the medical implant. A radio-lucent material can then be injected into the mold to form a trial implant. A person having ordinary skill in the art will appreciate that a variety of techniques can be utilized to manufacture a trial implant according to the present invention.

The materials used for form a trial implant according to the present invention can vary. Preferably, the body 12 is formed from a rigid, semi-rigid, or flexible radio-lucent material. More preferably, the body 12 is formed from materials such as polymers, ceramics, composite materials, and combinations thereof. Examples of suitable polymers include polyether sulfone, polycarbonate, and bioabsorbable polymers, and examples of suitable composites include carbon fiber reinforced polymers. The marker strip can also be formed from a variety of radio-opaque materials including, for example, metals, polymers, filling salts, ceramics, and combinations thereof. Examples of suitable metals include titanium, stainless steel, tantalum, cobalt chromium, aluminum, and combinations thereof. A person having ordinary skill in the art will appreciate that the body can be formed from a radio-opaque material, and the marker strip can be formed from a radio-lucent material.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A trial medical implant device, comprising:
   a body formed from a radio-lucent material and having a size and shape adapted to fit within or adjacent to an interstitial space; and
   a plurality of pairs of markers formed from a radio-opaque material, each pair being selectively positioned along a predetermined axis with respect to the body such that an x-ray visible reference of a pair of markers, taken along the predetermined axis, indicates the position and alignment of the body with respect to an anatomical structure when the trial medical implant device is positioned within an interstitial space.

2. The trial medical implant device of claim 1, wherein at least one of the markers is selectively distinguishable, on an x-ray image, from another one of the markers.

3. The trial medical implant device of claim 1, wherein each marker has a shape selected from the group consisting of an elongate strip, a tube, a cross, a sphere, a plate, a ring, a rod, a T-shape, and combinations thereof.

4. The trial medical implant device of claim 1, wherein each marker is disposed on an outer surface of the body or embedded in the body.

5. The trial medical implant device of claim 1, wherein at least one marker is disposed on an outer surface of the body and at least one marker is embedded in the body.

6. The trial medical implant device of claim 1, wherein the body has a shape and size adapted to fit between adjacent vertebral bodies.

7. The trial medical implant device of claim 6, wherein the body is a disc-shaped member having a superior, bone-contacting surface and an inferior, bone-contacting surface, and wherein the plurality of pairs of markers are effective to indicate the alignment of the superior and inferior bone-contacting surfaces of the body with respect to superior and inferior endplates of adjacent vertebral bodies when the implant is positioned between adjacent vertebral bodies.

8. The trial medical implant device of claim 1, wherein the body is formed from materials selected from the group consisting of polymers, ceramics, composite materials, and combinations thereof.

9. The trial medical implant device of claim 8, wherein the polymers are selected from the group consisting of polyether sulfone, polycarbonate, bioabsorbable polymers, carbon fiber reinforced polymers, and combinations thereof.

10. The trial medical implant device of claim 1, wherein each marker is formed from a material selected from the group consisting of metals, polymers, filling salts, ceramics, and combinations thereof.

11. The trial medical implant device of claim 10, wherein the metals are selected from the group consisting of titanium, stainless steel, tantalum, cobalt chromium, aluminum, and combinations thereof.

12. A trial spinal implant, comprising:
    a trial implant member formed from a radio-lucent material and having a size and shape configured to fit between adjacent vertebral bodies, the trial implant member including a superior bone-contacting surface and an inferior bone-contacting surface, each having a shape adapted to conform to an endplate of an adjacent vertebral body;
    a plurality of markers formed from a radio-opaque material and selectively associated with the trial implant member such that, when the trial implant is positioned between adjacent vertebral bodies, the plurality of markers intersect with one another to provide at least one x-ray visible reference to indicate the alignment of the superior and inferior bone-contacting surfaces of the implant member with respect to the endplates of the adjacent vertebral bodies.

13. The trial spinal implant of claim 12, wherein the plurality of markers are disposed on an outer surface of the trial implant member or are embedded in the trial implant member.

14. The trial spinal implant of claim 12, wherein at least one marker is disposed on an outer surface of the trial implant member and at least one marker is embedded in the trial implant member.

15. The trial spinal implant of claim 12, wherein the plurality of markers have a shape selected from the group consisting of an elongate strip, a tube, a cross, a sphere, a plate, a ring, a rod, a T-shape, and combinations thereof.

16. The trial spinal implant of claim 12, wherein the trial implant member is formed from materials selected from the group consisting of polymers, ceramics, composite materials, and combinations thereof.

17. The trial spinal implant of claim 16, wherein the polymers are selected from the group consisting of polyether sulfone, polycarbonate, bioabsorbable polymers, carbon fiber reinforced polymers, and combinations thereof.

18. The trial spinal implant of claim 12, wherein the plurality of markers are formed from a material selected from the group consisting of metals, polymers, filling salts, ceramics, and combinations thereof.

19. The trial spinal implant of claim 18, wherein the metal is selected from the group consisting of titanium, stainless steel, tantalum, cobalt chromium, aluminum, and combinations thereof.

20. The trial spinal implant of claim 12, wherein the plurality of markers comprises at least one pair of markers positioned along a predetermined axis and configured such that an x-ray image of the markers, taken along the predetermined axis indicates the alignment of the implant.

21. A trial implant system, comprising:
    a plurality of implantable trial prostheses, each implantable prosthesis having a different size and comprising
        a body formed from a radio-lucent material and having a size and shape adapted to fit within or adjacent to an anatomical structure, and
        a plurality of markers selectively associated with the body and formed from a radio-opaque material, the plurality of markers intersecting one another to provide at least one x-ray visible reference point to indicate the position and alignment of the body with respect to the anatomical structure when the implantable trial prosthesis is positioned within an anatomical structure.

22. The trial implant system of claim 21, wherein the body of each implantable trial prosthesis includes superior and inferior bone-contacting surfaces, each having a shape adapted to conform to an endplate of a vertebral body, and wherein the plurality of markers indicate, on an x-ray image, the alignment of the superior and inferior bone-contacting surfaces of the body with respect to the endplates of adjacent vertebral bodies when the implantable trial prosthesis is positioned within an anatomical structure.

23. The trial implant system of claim 21, wherein the plurality of markers are disposed on an outer surface of the body or is embedded in the body.

24. The trial implant system of claim 21, wherein at least one marker is disposed on an outer surface of the body and at least one marker is embedded in the body.

25. The trial implant system of claim 21, wherein the plurality of markers have a shape selected from the group consisting of an elongate strip, a tube, a cross, a sphere, a plate, a ring, a rod, a T-shape, and combinations thereof.

26. The trial implant system of claim 21, wherein the body is formed from materials selected from the group consisting of polymers, ceramics, composite materials, and combinations thereof.

27. The trial implant system of claim 26, wherein the polymers are selected from the group consisting of polyether sulfone, polycarbonate, bioabsorbable polymers, carbon fiber reinforced polymers, and combinations thereof.

28. The trial implant system of claim 21, wherein the plurality of markers are formed from a material selected from the group consisting of metals, polymers, filling salts, ceramics, and combinations thereof.

29. The trial implant system of claim 28, wherein the metal is selected from the group consisting of titanium, stainless steel, tantalum, cobalt chromium, aluminum, and combinations thereof.

30. A method for manufacturing a trial spinal implant, comprising:
    providing a plurality of markers formed from a radio-opaque material;
    providing a mold for a substantially disc-shaped spinal implant having superior and inferior bone-contacting surfaces, each having a shape adapted to conform to an endplate of an adjacent vertebral body;
    strategically placing each of the plurality of markers in the mold such that the markers are configured to intersect one another to provide at least one x-ray visible reference point to indicate the alignment of the superior and inferior bone-contacting surfaces of the spinal implant with respect to the endplates of the adjacent vertebral bodies; and
    injecting a radio-lucent material into the mold to form a trial implant.

* * * * *